US010462444B2

(12) United States Patent
Wolke et al.

(10) Patent No.: US 10,462,444 B2
(45) Date of Patent: Oct. 29, 2019

(54) THREE-DIMENSIONAL INSPECTION

(71) Applicant: FARO Technologies, Inc., Lake Mary, FL (US)

(72) Inventors: Matthias Wolke, Korntal-Münchingen (DE); Bernd-Dietmar Becker, Ludwigsburg (DE)

(73) Assignee: FARO TECHNOLOGIES, INC., Lake Mary, FL (US)

( * ) Notice: Subject to any disclaimer, the term of this patent is extended or adjusted under 35 U.S.C. 154(b) by 0 days.

(21) Appl. No.: 15/926,114

(22) Filed: Mar. 20, 2018

(65) Prior Publication Data
US 2018/0302605 A1    Oct. 18, 2018

Related U.S. Application Data

(60) Provisional application No. 62/486,102, filed on Apr. 17, 2017.

(51) Int. Cl.
*H04N 13/122* (2018.01)
*H04N 13/254* (2018.01)
(Continued)

(52) U.S. Cl.
CPC ......... *H04N 13/122* (2018.05); *G01B 11/002* (2013.01); *G01B 11/24* (2013.01); *G01B 11/245* (2013.01); *G01N 21/8806* (2013.01); *G01N 21/9515* (2013.01); *G02B 27/106* (2013.01); *G02B 27/126* (2013.01); *G06T 7/55* (2017.01); *H04N 13/243* (2018.05); *H04N 13/254* (2018.05); *G01B 2210/58* (2013.01); *G01N 2021/217* (2013.01); *G01N 2021/845* (2013.01); *G01N 2021/8848* (2013.01); *G06T 7/0004* (2013.01); *G06T 2207/10012* (2013.01); *G06T 2207/30164* (2013.01)

(58) Field of Classification Search
CPC .. H04N 13/122; H04N 13/254; H04N 13/243; H04N 13/337; H04N 13/20; G06T 7/55; G06T 7/0004; G06T 2207/10012; G06T 2207/30164; G01B 11/002; G01B 11/24; G01B 11/245; G01B 2210/58; G01N 21/21; G01N 2021/217; G02B 27/106; G02B 27/126; G02B 27/26
USPC ....... 348/42, 46–50; 382/154; 345/419, 653, 345/664; 359/462, 465, 475
See application file for complete search history.

(56) References Cited

U.S. PATENT DOCUMENTS

| 5,768,792 A | 6/1998 | Raab |
| 5,926,268 A | 7/1999 | Bonewitz et al. |

(Continued)

FOREIGN PATENT DOCUMENTS

| JP | 2010197370 A | 9/2010 |
| WO | 2016174915 A1 | 11/2016 |

OTHER PUBLICATIONS

Moxtek, "Wire-Grid Pixelated Polarizers" (Jan. 1, 2015), XP055484126, Retrieved from Internet: URL:https://qd-uki.co.uk/admin/images/uploaded_images/[Wire-Grid-pixelated-polarisers] Pixelated-Polarizers-OPT-DATA-1005-Rev-E.pdf (2 pgs).

(Continued)

*Primary Examiner* — Sherrie Hsia
(74) *Attorney, Agent, or Firm* — Cantor Colburn LLP

(57) ABSTRACT

A method of determining machined characteristics of a surface with a camera system, the camera system operable to obtain six camera images. The camera images are formed by illuminating the surface with light at each of two different angles. After reflecting off the surface, the light is passed through a polarizer at each of three different angles.

15 Claims, 10 Drawing Sheets

(51) Int. Cl.
  *H04N 13/243*   (2018.01)
  *G02B 27/10*    (2006.01)
  *G02B 27/12*    (2006.01)
  *G01B 11/00*    (2006.01)
  *G01B 11/24*    (2006.01)
  *G01B 11/245*   (2006.01)
  *G06T 7/55*     (2017.01)
  *G01N 21/88*    (2006.01)
  *G01N 21/95*    (2006.01)
  *G06T 7/00*     (2017.01)
  *G01N 21/21*    (2006.01)
  *G01N 21/84*    (2006.01)

(56) References Cited

U.S. PATENT DOCUMENTS

| | | |
|---|---|---|
| 5,978,748 A | 11/1999 | Raab |
| 6,868,359 B2 | 3/2005 | Raab |
| 6,879,933 B2 | 4/2005 | Steffey et al. |
| 7,006,084 B1 | 2/2006 | Buss et al. |
| 7,246,030 B2 | 7/2007 | Raab et al. |
| 8,760,517 B2 * | 6/2014 | Sarwar .............. G01J 4/00 348/156 |
| 2004/0257565 A1 | 12/2004 | Ishihara |
| 2010/0289878 A1 | 11/2010 | Sato et al. |
| 2011/0102793 A1 | 5/2011 | Straaijer |
| 2013/0028474 A1 | 1/2013 | Silver |
| 2013/0197852 A1 | 8/2013 | Grau et al. |
| 2015/0054946 A1 | 2/2015 | Zhang |
| 2015/0178412 A1 | 6/2015 | Grau |
| 2015/0330764 A1 | 11/2015 | Gong |
| 2016/0077515 A1 | 3/2016 | Pfeffer et al. |
| 2016/0261844 A1 | 9/2016 | Kadambi et al. |
| 2016/0284079 A1 | 9/2016 | Persely |

OTHER PUBLICATIONS

Extended European Search Report for Application No. 18167100.9 dated Jun. 29, 2018; 10 pgs.

* cited by examiner

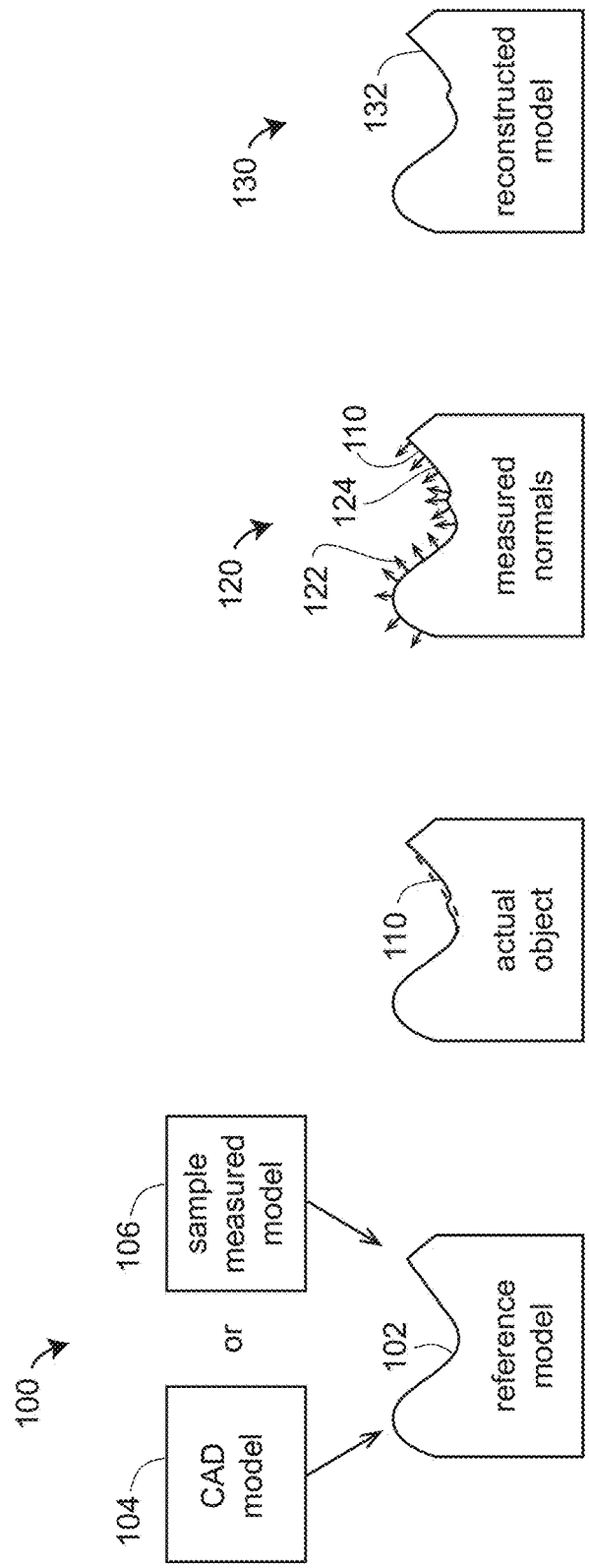

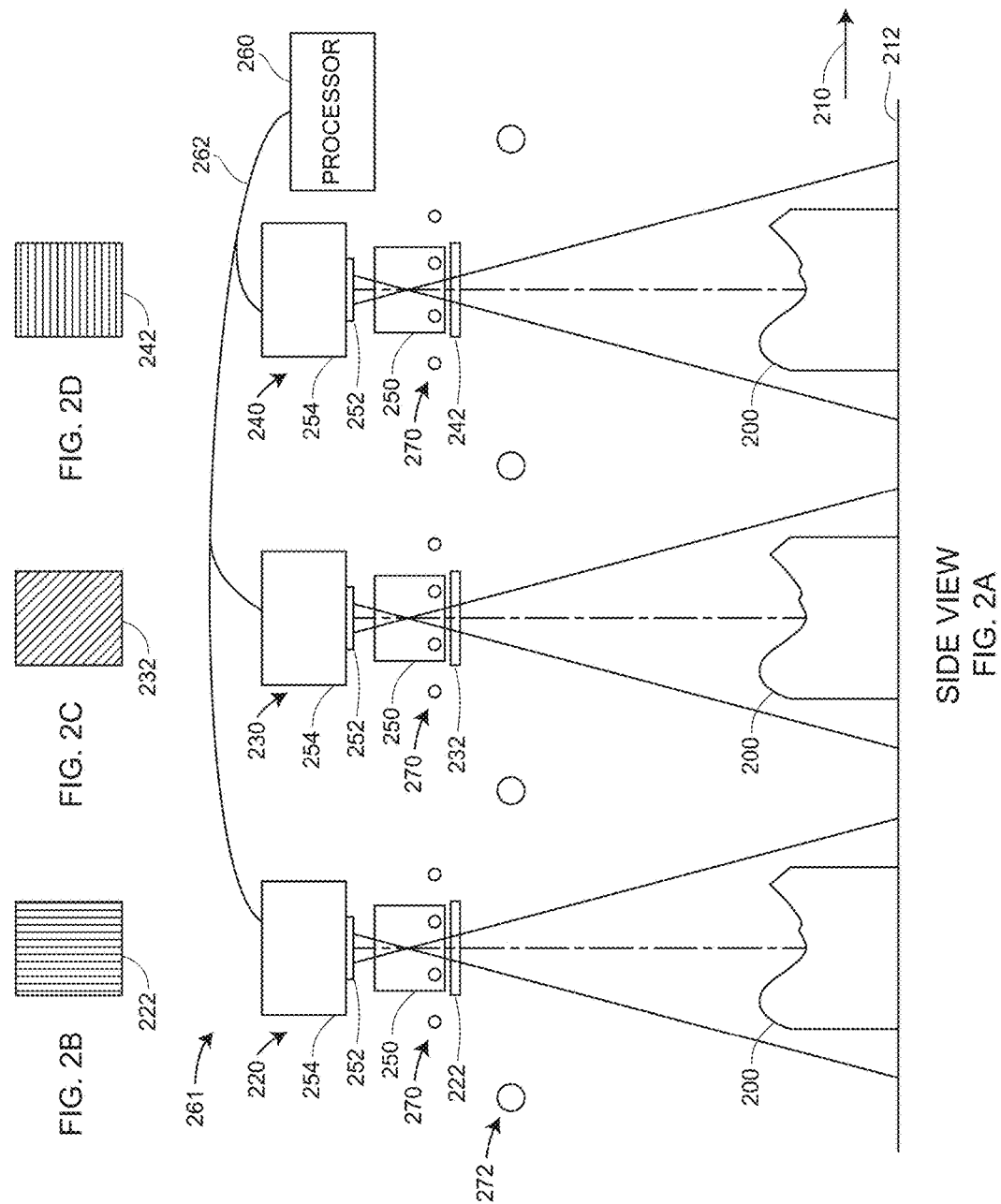

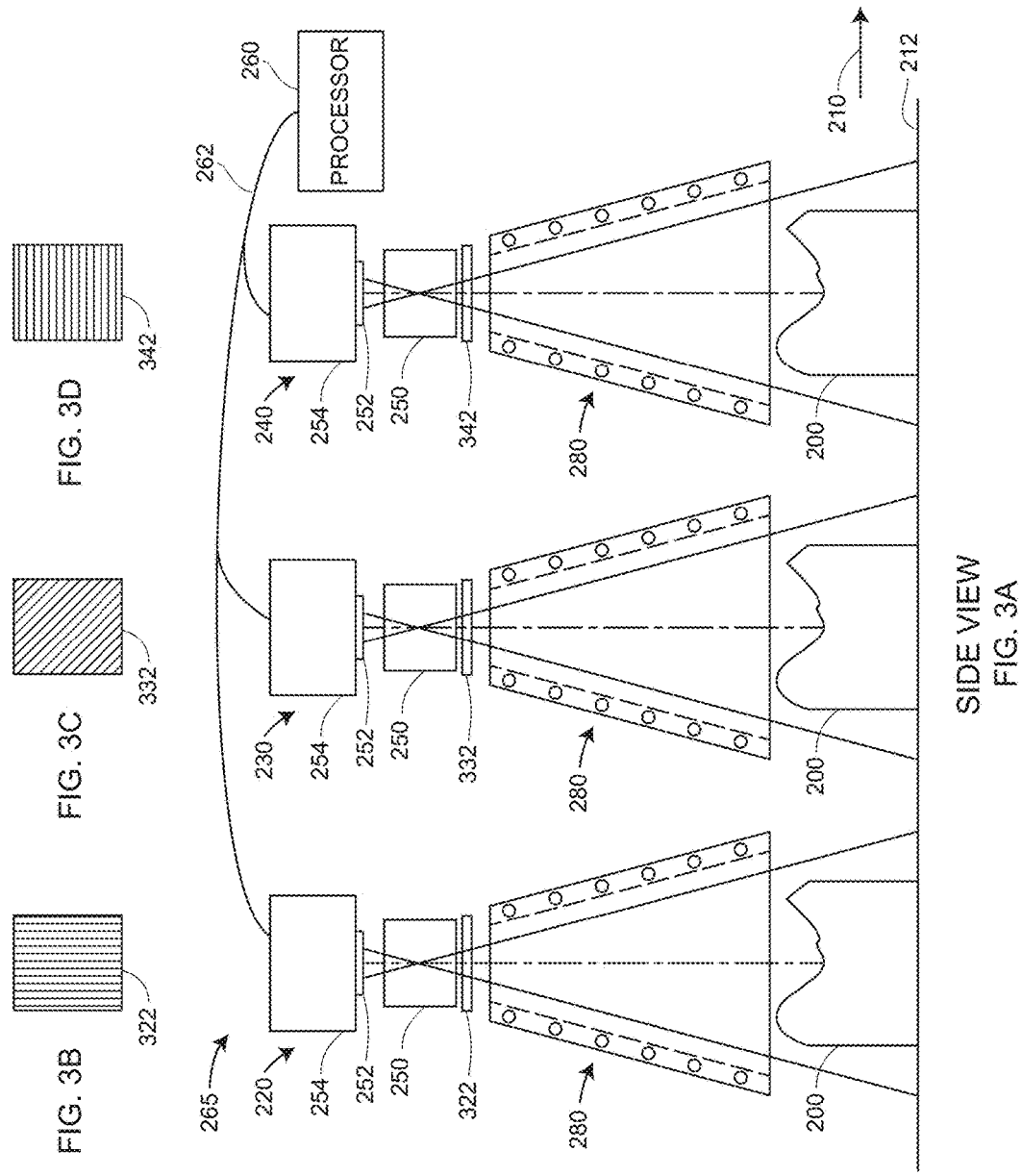

SIDE VIEW

SIDE VIEW

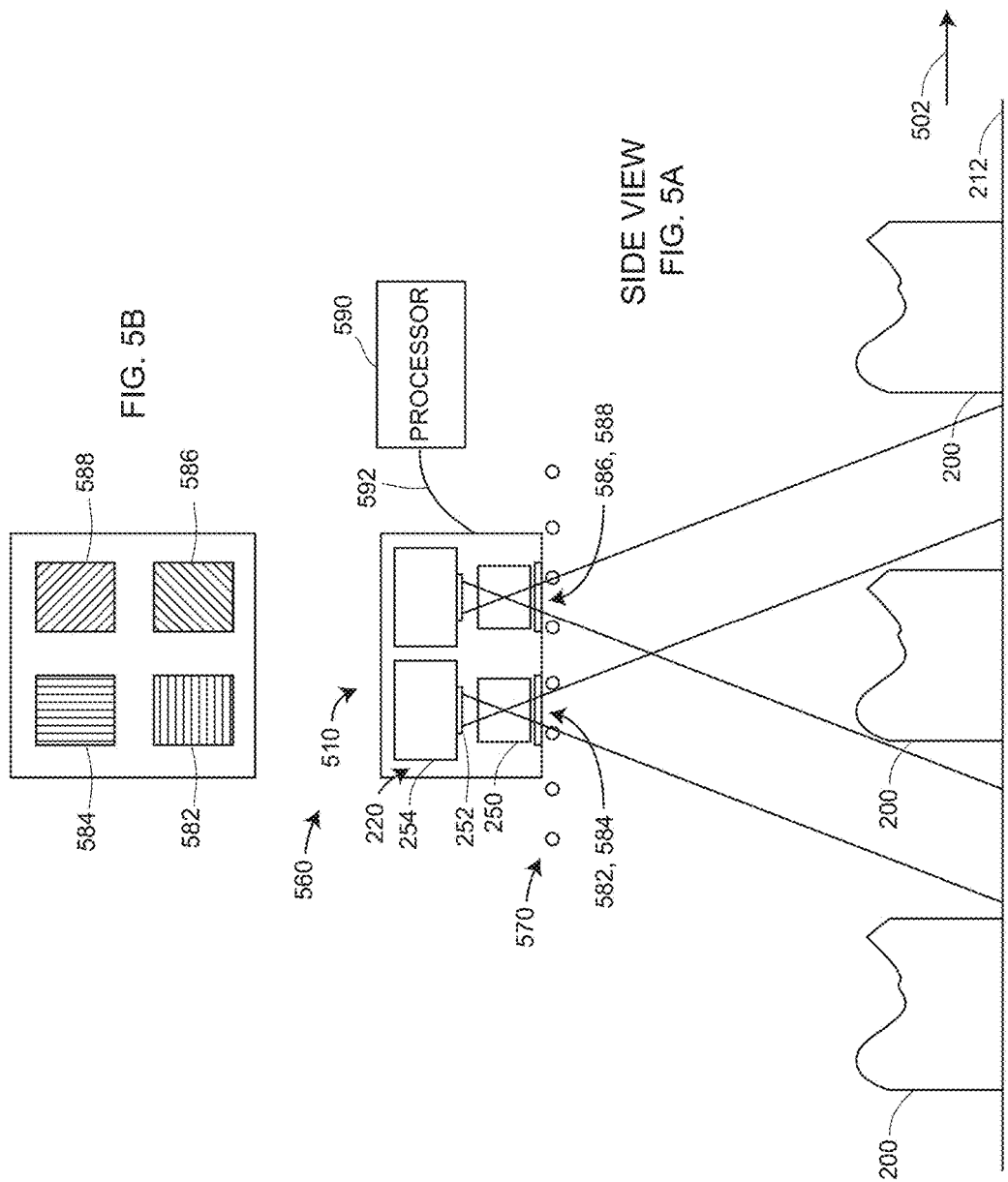

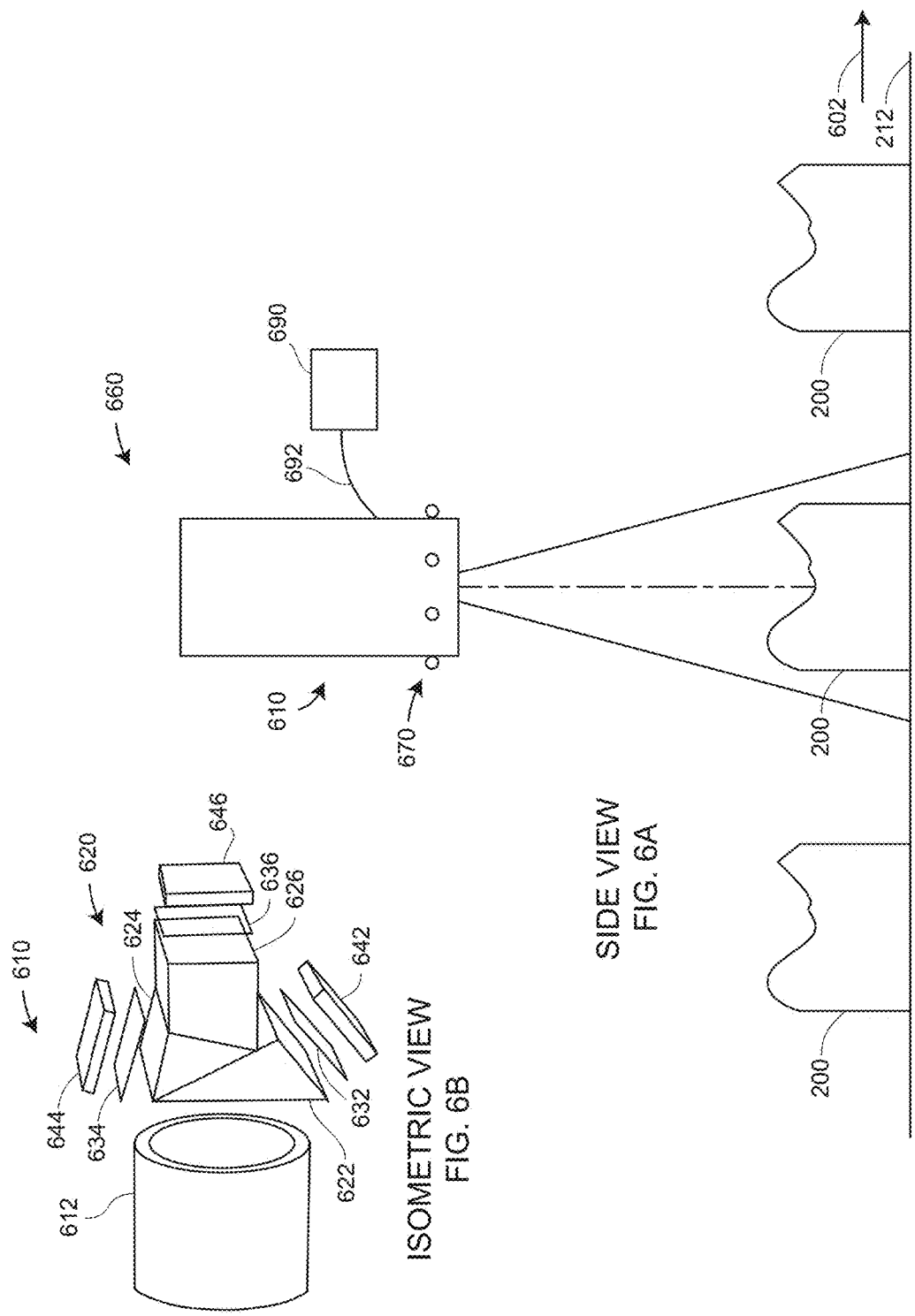

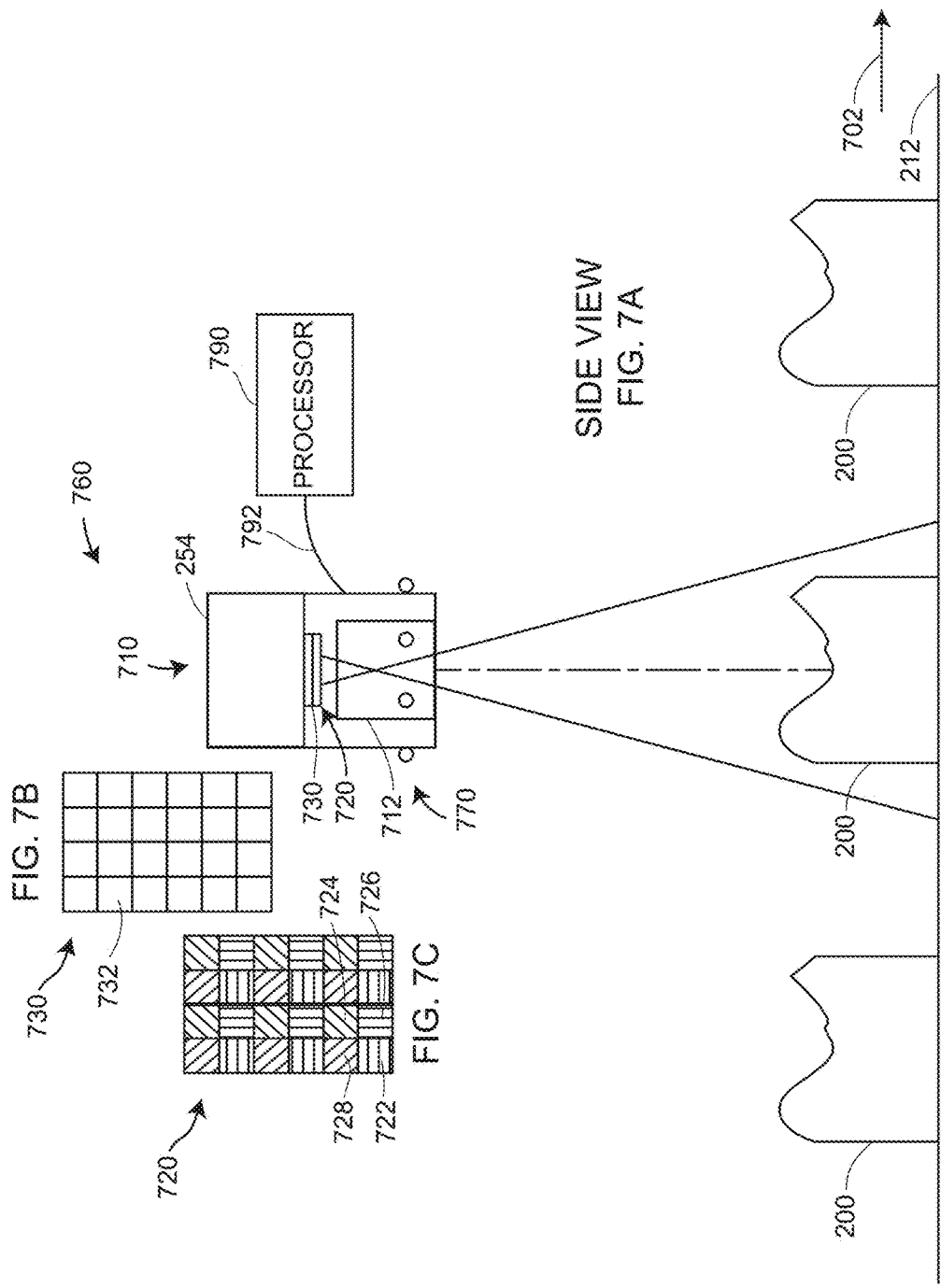

FIG. 8C: 70° S0
FIG. 9C: −45° S0
FIG. 8B: 70° DOLP
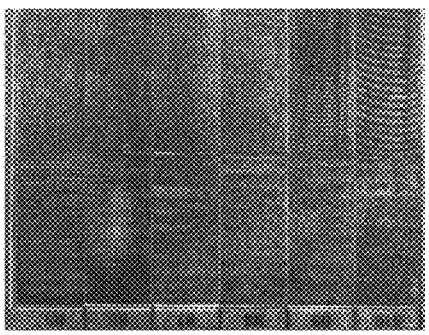
FIG. 9B: −45° DOLP
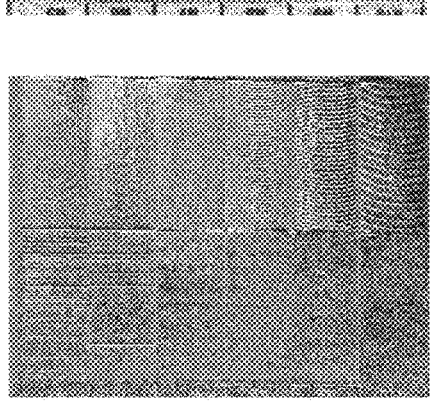
FIG. 8A: 70° AOP
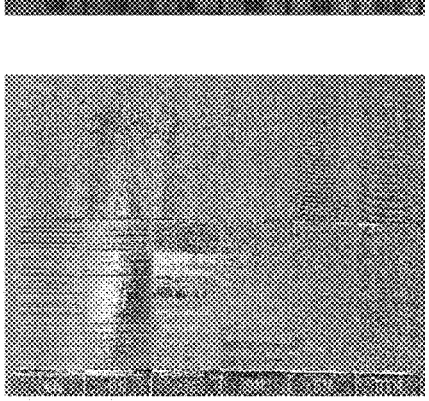
FIG. 9A: −45° AOP

THREE-DIMENSIONAL INSPECTION

CROSS REFERENCE TO RELATED APPLICATIONS

The present application is a nonprovisional application of U.S. Provisional Application Ser. No. 62/486,102 filed on Apr. 17, 2017, the contents of which are incorporated herein by reference in their entirety.

FIELD OF THE INVENTION

The subject matter disclosed herein relates in general to three-dimensional (3D) inspection using cameras and polarizers.

BACKGROUND

In many cases, automated inspection of manufactured objects seeks to find deviations from a 3D model of each inspected object. The 3D model may, for example, be a computer-aided design (CAD) model or a model based on previously measured 3D coordinates of a sample object. It may be desirable in such inspections to perform such 3D inspections rapidly, with adequate accuracy, and with relatively low cost in inspection test equipment.

Accordingly, while existing automated 3D inspection systems are suitable for their intended purpose, the need for improvement remains.

BRIEF DESCRIPTION

According to an embodiment of the present invention, a method for measuring three-dimensional (3D) coordinates of a first object comprises: providing a reference model of the first object; providing at least one processor; providing a camera system having a first linear polarizer oriented at a first angle, a second linear polarizer oriented at a second angle, and a third linear polarizer oriented at a third angle; forming with the camera system a first image of the first object seen through the first linear polarizer and sending a first electrical signal to the at least one processor in response; forming with the camera system a second image of the first object seen through the second linear polarizer and sending a second electrical signal to the at least one processor in response; forming with the camera system a third image of the first object seen through the third linear polarizer and sending a third electrical signal to the at least one processor in response; determining by the at least one processor the 3D coordinates of the first object based at least in part on the reference model, the first electrical signal, the second electrical signal, the third electrical signal, the first angle, the second angle, and the third angle; and storing the 3D coordinates.

According to a further embodiment of the present invention, another system for measuring three-dimensional (3D) coordinates is provided. The system includes a camera system having a first linear polarizer oriented at a first angle, a second linear polarizer oriented at a second angle, and a third linear polarizer oriented at a third angle. The first camera system is operable to form a first image of the first object as seen through the first linear polarizer and sending a first electrical signal in response. The second camera system is operable to form a second image of the first object as seen through the second linear polarizer and sending a second electrical signal in response. The third camera system is operable to form a third image of the first object as seen through the third linear polarizer and sending a third electrical signal in response. The system further includes a processor operable to determine the 3D coordinates of the first object based at least in part on a reference model, the first electrical signal, the second electrical signal, the third electrical signal, the first angle, the second angle, and the third angle.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings in which:

FIGS. 1A, 1B, 1C, 1D together provide a schematic representation of stages in the determining of 3D object coordinates according to an embodiment of the present invention;

FIGS. 2A, 2B, 2C, 2D are schematic representations of objects transported on a conveyor belt and measured sequentially by 2D cameras having linear polarizers according to an embodiment of the present invention;

FIGS. 3A, 3B, 3C, 3D are schematic representations of objects transported on a conveyor belt and measured sequentially by 2D cameras having linear polarizers according to an embodiment of the present invention;

FIGS. 5A, 5B are schematic representations of objects measured by a 2D camera assembly having three or more cameras, each with a polarizer according to an embodiment of the present invention;

FIG. 6A is a schematic representation of moving objects measured by a 2D camera assembly having a prism that sends light to three or more cameras, each camera including a polarizer according to an embodiment of the present invention;

FIG. 6B is a perspective view of a camera and polarizer assembly according to an embodiment of the present invention;

FIGS. 7A, 7B, 7C is a schematic representation of moving objects measured by a 2D camera assembly having a polarizer array matched to pixels in a photosensitive array according to an embodiment of the present invention;

FIGS. 8A, 8B, 8C are processed image data that yields angle of polarization (AOP), degree of linear polarization (DOLP), and optical intensity (S0) for a metal plate illuminated at 70 degrees, according to an embodiment of the present invention;

FIGS. 9A, 9B, 9C are processed image data that yields angle of polarization (AOP), degree of linear polarization (DOLP), and optical intensity (S0) for a metal plate illuminated at −45 degrees, according to an embodiment of the present invention.

Figure 4A:
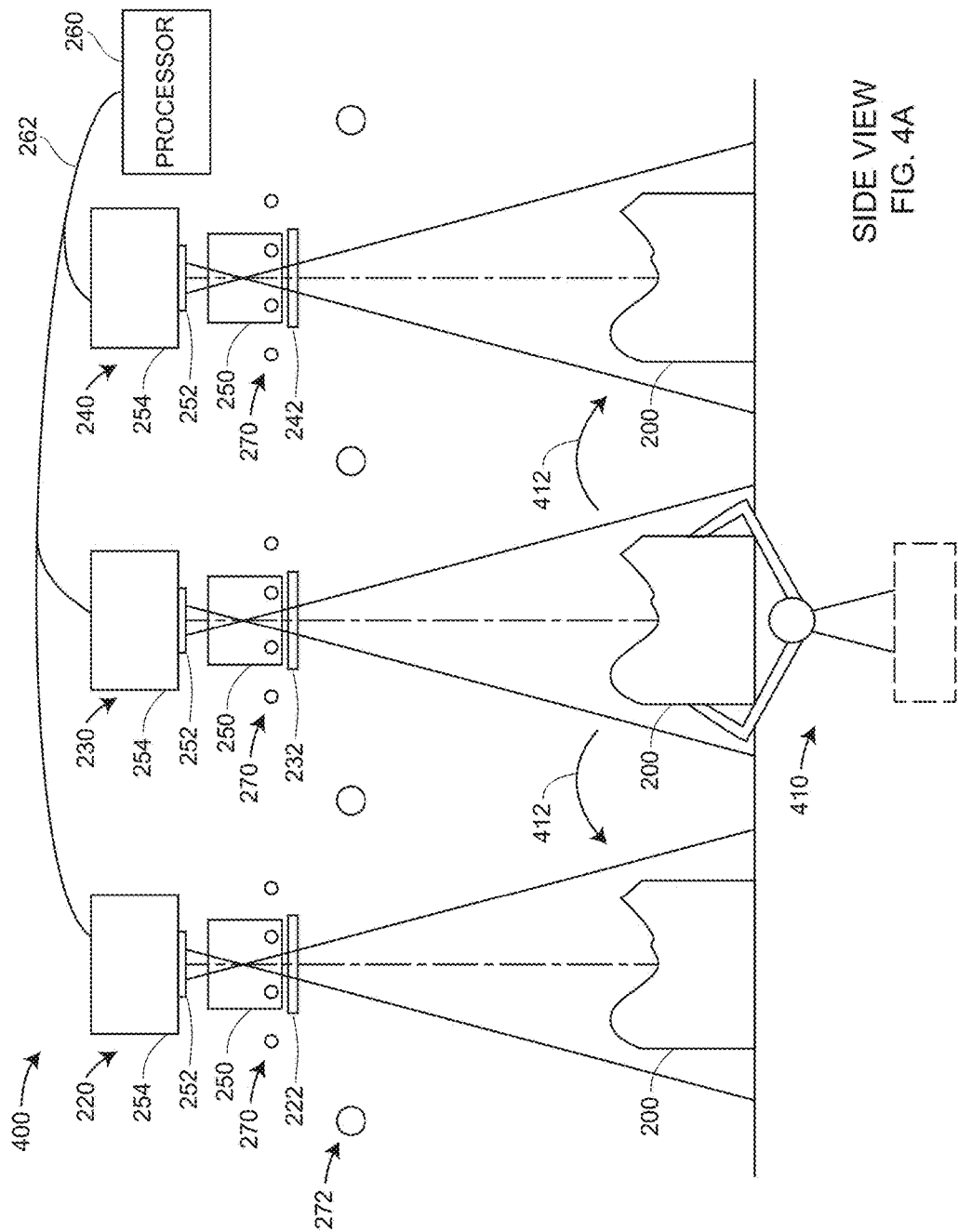
FIGS. 4A, 4B are schematic representations of objects transported on a robot and measured sequentially by 2D cameras having linear polarizers according to an embodiment of the present invention.

The detailed description explains embodiments of the invention, together with advantages and features, by way of example with reference to the drawings.

DETAILED DESCRIPTION

Embodiments of the present invention provide advantages measuring 3D coordinates relatively rapidly, with relatively high accuracy and at relatively low cost.

FIGS. 1A, 1B, 1C, 1D illustrate stages of a 3D inspection procedure according to an embodiment of the present invention. In a first stage 100 of the 3D inspection procedure, a reference model 102 is provided. In an embodiment, the reference model 102 is a CAD model 104 or other provided electronic 3D model. In another embodiment, the reference model is a sample measured model 106—that is, measured 3D values of a sample object. Any type of 3D measuring device may be used to collect the 3D measured values of the sample measured model 106. In an embodiment, the 3D measuring device may be, but is not limited to, an optical triangulation scanner for example. FIG. 1B shows an example of an actual object 110 which, in general, differs in some ways from the reference model 102. In a stage 120 illustrated in FIG. 1C, cameras and polarizers are used together to measure normal vectors 122 to the surface 124 of the actual object 110 according to methods described further herein below. In a stage 130 (FIG. 1D), the measured normal vectors 122 are merged with the reference model 102 to obtain a reconstructed model 132, which more accurately represents the 3D coordinates of the actual object 110 than does the reference model 102.

In embodiments illustrated in FIG. 2A and 3A, an object 200 travels along a path 210 on a moving track or conveyor belt 212. In an embodiment, each object 200 passes sequentially under a collection of cameras 220, 230, 240. Each camera 220, 230, 240 includes a lens system 250, a photosensitive array 252, and camera electronics 254. In an embodiment, the camera electronics 254 are connected to a processor or computer 260, which might be an external computer or networked computer. The signals from the camera electronics 254 may be sent to the computer 260 over a communications medium or channels 262 that are either wired or wireless. The terms processor and computer as used herein should be understood to include volatile and non-volatile memory for storage of data as well as computational electronics. In other embodiments, processors may be included in the camera electronics 254. In an embodiment, the cameras 220, 230, 240 further include a linear polarizer 222, 232, 242, respectively, shown in FIGS. 2B, 2C, 2D. In the embodiment, of FIG. 3A, 3B, 3C, 3D, the cameras 220, 230, 240 include linear polarizers 322, 332, 342 respectively. In an embodiment, each linear polarizer is rotated to a different angle. In the embodiments illustrated in FIGS. 2B, 2C, 2D, 3B, 3C, 3D, the linear polarizers are rotated to angles of 0, 45, and 90 degrees. In other embodiments, the linear polarizers are rotated to other angles such as 0, 120, and 240 degrees. In other embodiments, other angles are selected. In other embodiments, one or more additional cameras are included in the 3D inspection system. The inspection system 261 of FIG. 2A and the inspection system 265 of FIG. 3A differ in the illumination system each employs. In an embodiment, the inspection system 261 relies on dedicated light sources 270, which in an embodiment are affixed to the camera assemblies 220, 230, 240 and in another embodiment are diffusely applied from general room lighting 272. In an embodiment, the inspection system 265 of FIG. 3A relies on lights 280 positioned to illuminate each object from a wide range of different angles.

Figure 10A:
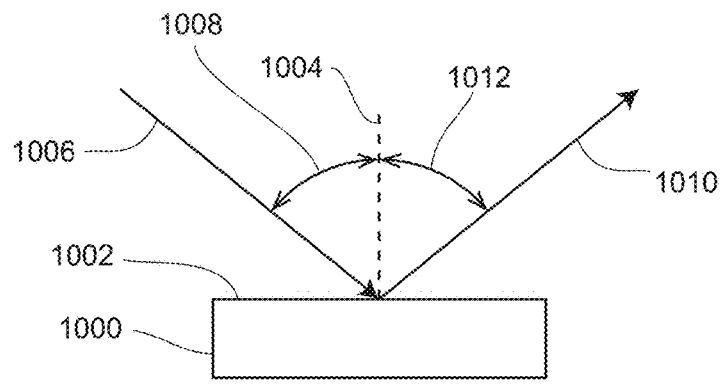
FIGS. 10A, 10B, 10C shows types of reflections that may occur for different types of surfaces.

Different types of materials respond differently to incident light. FIG. 10A shows a material 1000 having a smooth surface 1002 with a normal direction 1004. An incoming ray of light 1006 arrives an angle of incidence 1008 and is reflected as a ray of light 1010 at an angle of reflection 1012 equal to the angle of incidence 1008. Reflection in which a collimated beam of light on a surface reflects almost entirely in the same direction as in FIG. 10A is referred to as specular reflection. Such specular reflections may be seen, for example, in polished metal and in some dielectric materials.

Figure 10B:
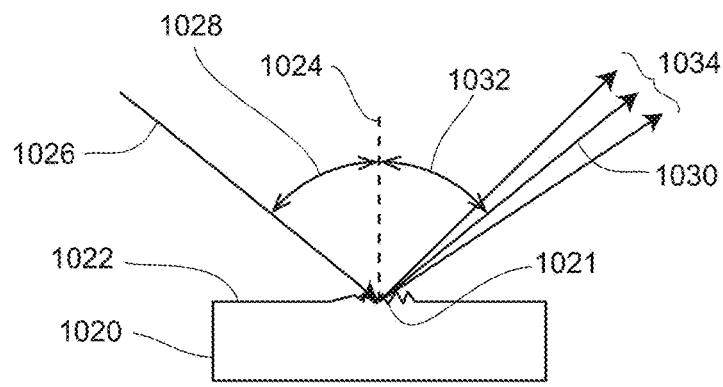

FIG. 10B shows a material 1020 having a surface 1022 with a finish that has some surface roughness features 1021. An incoming ray of light 1026 arrives at an angle of incidence 1028 and reflects from a normal 1024 as a reflected ray 1030 having an angle of reflection 1032 equal to the angle of incidence 1026. However, because of the surface roughness, the direction of the normal 1024 varies from location to location on the surface 1022, resulting in reflection of a bundle of ray 1034 spread over a range of angles. This type of reflection or scattering is seen for example in metals having a matte finish following machining and it is also seen in some finished dielectric materials.

Figure 10C:
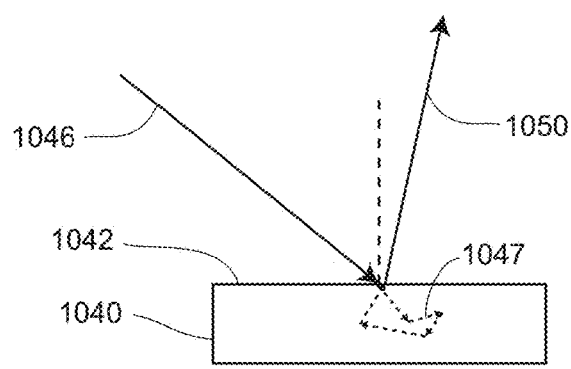

FIG. 10C shows a material 1040 having a surface 1042 that may be smooth or rough. Part of an incoming ray of light 1046 penetrates the surface 1042 and undergoes a scattering process 1047 that results in depolarization of the light. The emerging light has its polarization modified, at least slightly, by the Fresnel equations that govern refraction and reflection. The emerging ray of light 1050 will not in general have an angle of reflection equal to the angle of incidence. Such scattering processes are typically seen in dielectric materials rather than metals. However, scattered light from a dielectric material is usually not completely depolarized.

In an embodiment, the lighting 280 illustrated in FIG. 3A is applied to an object 200 made of metal. Light is reflected from the metal surface according to the Fresnel Equations, with the angle of reflection equal to the angle of incidence. For this reason, metals are said to exhibit "interface reflection," where the interface is the air-metal interface of the object 200. If the metal surface is relatively rough, the metal surface may be regarded as including a collection of small metal facets, each facet exhibiting an interface reflection. Most metals have some degree of roughness, which causes a finite beam of collimated light incident on a metal surface to be reflected in a range of directions, resulting in light sometimes said to be "diffusely reflected" or "diffusely scattered." When determining the normal vectors to a metal surface using the methods described herein, in an embodiment, the metal surface is illuminated from a wide range of directions. In the ideal case, incident light is provided that illuminates the metal surface omnidirectionally.

An example of the effect of illuminating a metallic surface by light arriving at a single angle of incidence is illustrated in FIGS. 8A, 8B, 8C, 9A, 9B, 9C. In FIGS. 8A, 8B, 8C, a machined metal plate is illuminated by light arriving at an angle of incidence of 70 degrees. In FIGS. 9A, 9B, 9C, the same machined metal plate is illuminating by light arriving at an angle of incidence of −45 degrees. For each of the two angles of incidence, three different images were obtained by sequentially placing linear polarizers in front of a camera, with the three linear polarizers oriented at three different angles—in the example shown in FIGS. 8A, 8B, 8C, 9A, 9B, 9C.

In an embodiment, the three or more images are processed to determine an angle of polarization (AOP) as shown in FIGS. 8A, 9A and a degree of linear polarization (DOLP) as shown in FIGS. 8B, 9B. In an embodiment, azimuthal components of normal vectors to the object surface are determined based on the AOP for each pixel of the AOP image of FIGS. 8A, 9A. In an embodiment, zenith components of the normal vectors are determined based on the degree of linear polarization (DOLP) for each pixel of the DOLP image of FIGS. 8B, 9B. A description of such calculations is given in Kadambi, et al., "Polarized 3D: High-quality depth sensing with polarization cues," International Conference on Computer Vision, 2015, the contents of which are incorporated by reference herein. It is further possible to determine from the three polarization images a derived image showing light intensity on a pixel-by-pixel basis, as illustrated in FIGS. 8C, 9C. This pixel values in this derived image are also referred to as a grayscale values or values of the first Stokes parameter S0.

The metal plate of FIGS. 8A, 8B, 8C, 9A, 9B, 9C includes ten sections, each section machined using a different method. In addition, there is a label on the left side of the plate. Because of the different angles of illumination, there are differences in the AOPimages of FIGS. 8A, 9A. These differences will result in different calculated values for azimuth components of the normal vectors to the metal surface. Likewise, because of the different angles of illumination, there are differences in the DOLP images of FIGS. 8B, 9B. These differences will result in different calculated values for the zenith components of the normal vectors to the metal surface. The differences in FIG. 8A compared to FIG. 9A and the differences in FIG. 8B compared to FIG. 9B show that errors in the determined normal vectors may result when illumination is not applied from all directions.

In contrast to metals that exhibit interface reflection, many other types of materials, including many dielectrics, exhibit "body reflection," possibly in combination with interface reflection. Body reflection occurs when light penetrates past the air-material interface to enter the body of the material. Light in the body of the material may be scattered at one or more internal sites within material. When the light emerges from the air-material interface as reflected light (also referred to as scattered light), it will generally emerge at an angle of reflection not equal to the angle of incidence. The reflected (scattered) light is said to be diffusely reflected or diffusely scattered. Although the expression "diffuse reflection" is used both for metals and dielectric materials, the degree of angular spread in materials exhibiting body reflection will usually be much greater than for metals that exhibit only interface reflection. Consequently, when carrying out polarization-reflection measurements on materials having substantial body reflection, it is often possible perform the process without omnidirectionally illuminating the material surface. FIG. 1A shows two types of illumination, dedicated light sources 270 and diffusely applied general room light 272, which in embodiments are applied to materials that exhibit body reflection.

Figure 4B:
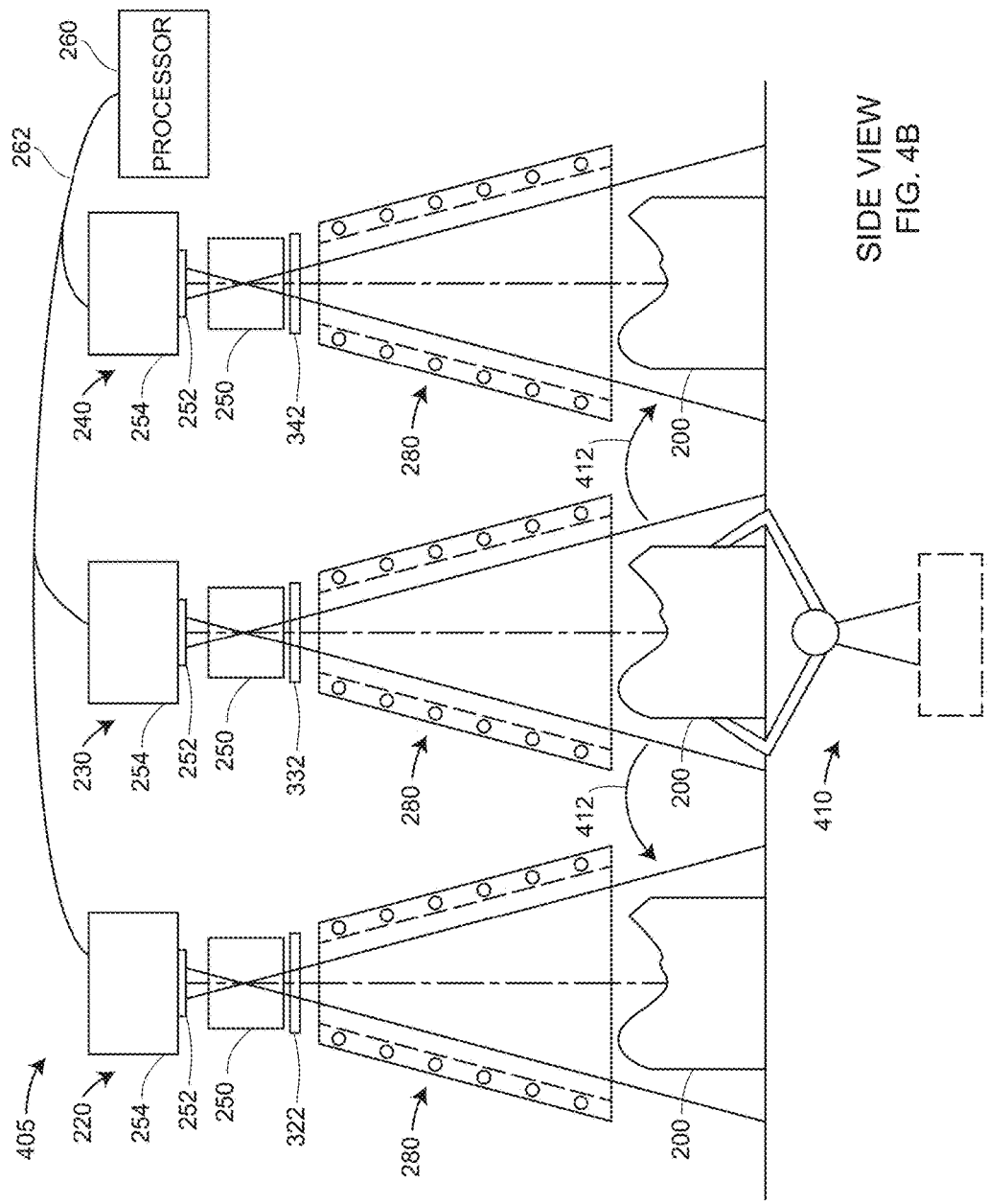

FIGS. 4A, 4B illustrate the same inspection methods 400, 405, respectively that are the same as the inspection methods shown in FIGS. 2A, 3A, respectively, except that the movement 210 of the conveyor belt 212 is replaced by the movement 412 of a robot 410.

FIGS. 5A, 5B are a schematic representation of an inspection system 560. In an embodiment, a camera assembly 510 includes four cameras 220, each camera having one of the polarizers 582, 584, 586, 588. In an embodiment, the four polarizers are linear polarizers, each oriented at a different angle. In further embodiments, a different number of cameras and polarizers are used. For example, three polarizers and three cameras may be used rather than four. In an embodiment, movement 502 of each object 200 is obtained through use of a conveyor belt 212. In another embodiment, the movement 502 is obtained through use of a robot 410 (FIGS. 4A, 4B). If metals are measured, the light system 570 may apply light omnidirectionally, for example, in a manner similar to the light system 280 of FIG. 3A. In another embodiment, the light system 570 may apply light in a different pattern, for example, in a manner similar to the light system 270 or 272 of FIG. 2A. Electrical signals are sent from the cameras 220 through a wired or wireless communication medium or channel 592 to a processor 590 for processing of captured images.

FIGS. 6A, 6B illustrate an inspection system 660. In an embodiment, a camera assembly 610 includes a lens system 612 that directs light to a prism assembly 620 that includes prism elements 622, 624, 626. The prism elements 622, 624, 626 separate the incoming light into three parts. A first part of the light passes through prism element 622 and a first polarizer 632 before forming an image on a photosensitive array 642. A second part of the light passes through the prism element 624 and a second polarizer 634 before forming an image on a photosensitive array 644. A third part of the light passes through the prism element 626 and a third polarizer 636 before forming an image on a photosensitive array 646. In an embodiment, movement 602 of each object 200 is obtained through use of a conveyor belt 212. In another embodiment, the movement 602 is obtained through use of a robot 410 (FIGS. 4A, 4B). If metals are measured, the light system 670 may apply light omnidirectionally, for example, in a manner similar to the light system 280 of FIG. 3A. In another embodiment, the light system 670 may apply light in a different pattern, for example, in a manner similar to the light system 270 or 272 of FIG. 2A. Electrical signals are sent from the photosensitive arrays 642, 644, 646 and their associated electronics over a wired or wireless communication medium or channel 692 to a processor 690 for processing of the collected images.

FIGS. 7A, 7B, 7C illustrate an inspection system 760. In an embodiment, a camera assembly 710 includes a lens system 712 that directs light through an array of linear polarizers 720 onto a photosensitive array 730 having pixels 732 that match the arrangement of polarizers in the array of linear polarizers. In the embodiment illustrated in FIG. 7C, the linear polarizers 722, 724, 726, 728 in the array of linear polarizers 720 are oriented at four different angles, 0, 45, 90, and 135 degrees. In other embodiments, different angles or different numbers of polarizers are used. In an embodiment, movement 702 of each object 200 is obtained through use of a conveyor belt 22. In another embodiment, movement 602 is obtained through use of a robot 410 (FIGS. 4A, 4B). If metals are measured, the light system 770 may apply light omnidirectionally, for example, in a manner similar to the light system 280 of FIG. 3A. In another embodiment, the light system 770 may apply light in a narrower pattern, for example, in a manner similar to the light system 270, 272 of FIG. 2A. Electrical signals are sent from the photosensitive array 730 and associated electronics over a wired or wireless communication medium or channel 792 to a processor 790 for processing of the collected image.

Communication among the computing (processing and memory) components may be wired or wireless. Examples of wireless communication methods include IEEE 802.11 (Wi-Fi), IEEE 802.15.1 (Bluetooth), and cellular communication (e.g., 3G, 4G, and 5G). Many other types of wireless communication are possible. A popular type of wired communication is IEEE 802.3 (Ethernet). In some cases, multiple external processors, such as network processors may be connected in a distributed computing configuration, such as cloud based computing. These network processors may be used to process scanned data in parallel, thereby providing faster results, especially where relatively time-consuming registration and filtering may be required.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method comprising:
providing at least one processor;
providing a camera system having a first linear polarizer oriented at a first angle, a second linear polarizer oriented at a second angle, and a third linear polarizer oriented at a third angle;
forming with the camera system a first image of a surface illuminated at a first angle and a second image of the surface illuminated at a second angle, the first image and the second image seen through the first linear polarizer;
forming with the camera system a third image of the surface illuminated at the first angle and a fourth image of the surface illuminated at the second angle, the third image and the fourth image seen through the second linear polarizer;
forming with the camera system a fifth image of the surface illuminated at the first angle and a sixth image of the surface illuminated at the second angle, the fifth image and the sixth image seen through the third linear polarizer;
with the at least one processor, determining machined characteristics of the surface based at least in part on the first image, the second image, the third image, the fourth image, the fifth image, and the sixth image; and
storing a description of the machined characteristics.

2. The method of claim 1, wherein the surface is a metallic surface.

3. The method of claim 1 further comprising:
determining by the at least one processor the machined characteristics further based on determining the angle of polarization (AOP) of the light reflected from the surface into the camera system.

4. The method of claim 1, wherein the camera system includes a first camera, a second camera, and a third camera, the first camera forming the first image and the second image, the second camera forming the third image and the fourth image, and the third camera forming the fifth image and the sixth image.

5. The method of claim 4, wherein the surface is part of an object.

6. The method of claim 5, wherein the object is measured sequentially by each of the first camera, the second camera, and the third camera.

7. The method of claim 6, wherein the object is moved by a moving platform.

8. The method of claim 6, wherein the object is moved by a robot.

9. The method of claim 1, wherein the camera system includes a prism beam splitter arranged to direct light to a first imaging unit, a second imaging unit, and a third imaging unit, the first imaging unit including the first linear polarizer disposed between the prism beam splitter and a first photosensitive array that captures the first image and the second image, the second imaging unit including the second linear polarizer disposed between the prism beam splitter and a second photosensitive array that captures the third image and the fourth image, the third imaging unit including the third linear polarizer disposed between the prism beam splitter and a third photosensitive array that captures the fifth image and the sixth image.

10. The method of claim 1, wherein the camera system includes a polarizer array, and a photosensitive array having a collection of pixels, the polarizer array including a collection of first polarizers, a collection of second polarizers, and a collection of third polarizers, the photosensitive array receiving the first image and the second image at a first subset of the collection of pixels, the third image and the fourth image at a second subset of the collection of pixels, and the fifth image and the sixth image at a third subset of the collection of pixels.

11. The method of claim 1 further comprising:
determining by the at least one processor the machined characteristics further based on determining the degree of linear polarization (DOLP) of the light reflected from the surface into the camera system.

12. The method of claim 1, wherein the first object is illuminated by light sources affixed to the camera system.

13. A system comprising:
a camera system having a first linear polarizer oriented at a first angle, a second linear polarizer oriented at a second angle, and a third linear polarizer oriented at a third angle, the camera system operable to form a first image of a surface illuminated at a first angle and a second image of the surface illuminated at a second angle, the first image and the second image being seen through the first linear polarizer, the camera system further operable to form a third image of the surface illuminated at the first angle and a fourth image of the surface illuminated at the second angle, the third image and the fourth image being seen through the second linear polarizer, the camera system further operable to form a fifth image of the surface illuminated at the third angle and a sixth image of the surface illuminated at the second angle, the fifth image and the sixth image being seen through the third linear polarizer; and
a processor operable to determine characteristics of the surface based at least in part on the first image, the second image, the third image, the fourth image, the fifth image, and the sixth image.

14. The system of claim 13, wherein the processor is operable to determine the characteristics of the surface further based on determining the angle of polarization (AOP) of the light reflected from the surface into the camera system.

15. The system of claim 14, wherein the processor is operable to determine the characteristics of the surface further based on determining the degree of linear polarization (DOLP) of the light reflected from the surface into the camera system.

* * * * *